(12) United States Patent
Griffin et al.

(10) Patent No.: US 8,973,239 B2
(45) Date of Patent: Mar. 10, 2015

(54) CATHETER HAVING AN ULTRA SOFT TIP AND METHODS FOR MAKING THE SAME

(75) Inventors: Stephen Griffin, San Jose, CA (US); Huey Quoc Chan, San Jose, CA (US); Elaine Lim, Fremont, CA (US); Lex P. Jansen, Pleasanton, CA (US); Anthony F. Tassoni, Jr., Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 940 days.

(21) Appl. No.: 12/906,884

(22) Filed: Oct. 18, 2010

(65) Prior Publication Data

US 2011/0035927 A1     Feb. 17, 2011

Related U.S. Application Data

(63) Continuation of application No. 11/009,667, filed on Dec. 10, 2004, now Pat. No. 7,815,599.

(51) Int. Cl.
*A61F 2/958* (2013.01)
*A61M 25/10* (2013.01)
*A61M 25/00* (2006.01)

(52) U.S. Cl.
CPC .......... *A61M 25/10* (2013.01); *A61M 25/0069* (2013.01); *A61M 2025/1093* (2013.01)
USPC ........................................... 29/428; 604/523

(58) Field of Classification Search
CPC ............................................. A61M 2025/1093
USPC .......... 29/428, 458, 525, 527.1, 527.2, 897.2; 264/259; 604/96–104, 523–530; 606/191–199
See application file for complete search history.

(56) References Cited

U.S. PATENT DOCUMENTS

| | | |
|---|---|---|
| 243,396 A | 6/1881 | Pfarre |
| 2,211,975 A | 8/1940 | Hendrickson |
| 2,407,929 A | 9/1946 | Jeckel |
| 2,437,542 A | 3/1948 | Krippendorf |
| 2,472,483 A | 6/1949 | Krippendorf |
| 3,174,851 A | 3/1965 | Buehler et al. |
| 3,351,463 A | 11/1967 | Rozner et al. |
| 3,416,531 A | 12/1968 | Edwards |
| 3,470,869 A | 10/1969 | Fenton et al. |
| 3,725,522 A | 4/1973 | Sheridan et al. |
| 3,734,100 A * | 5/1973 | Walker et al. ............ 128/207.15 |
| 3,753,700 A | 8/1973 | Harrison et al. |
| 3,757,768 A | 9/1973 | Kline |
| 3,865,666 A | 2/1975 | Shoney |
| 3,873,391 A | 3/1975 | Plauka et al. |
| 3,924,632 A | 12/1975 | Cook |

(Continued)

FOREIGN PATENT DOCUMENTS

| | | |
|---|---|---|
| DE | 3242449 | 5/1983 |
| DE | 3642107 | 6/1987 |

(Continued)

*Primary Examiner* — David Bryant
*Assistant Examiner* — Steven A Maynard
(74) *Attorney, Agent, or Firm* — Seager, Tufte & Wickhem, LLC

(57) ABSTRACT

An intravascular balloon catheter having an ultra soft tip. The catheter includes a braided reinforcement member extending substantially the length of the elongate shaft. A balloon is disposed at the distal end of the elongate shaft. An ultra soft tip is formed from a distal portion of balloon material extending distal of the distal end of the elongate shaft.

18 Claims, 4 Drawing Sheets

(56) References Cited

U.S. PATENT DOCUMENTS

| | | | |
|---|---|---|---|
| 3,959,429 | A | 5/1976 | Benning |
| 3,985,601 | A | 10/1976 | Panagrossi |
| 3,989,571 | A | 11/1976 | Harautuneian |
| 4,085,185 | A | 4/1978 | Adair |
| 4,093,484 | A | 6/1978 | Harrison et al. |
| 4,207,900 | A | 6/1980 | Patel et al. |
| 4,210,478 | A | 7/1980 | Shoney |
| 4,284,459 | A | 8/1981 | Patel et al. |
| 4,328,056 | A | 5/1982 | Snooks |
| 4,385,635 | A | 5/1983 | Ruiz |
| 4,395,806 | A | 8/1983 | Wonder et al. |
| 4,425,919 | A | 1/1984 | Alston, Jr. et al. |
| 4,430,083 | A | 2/1984 | Ganz et al. |
| 4,459,255 | A | 7/1984 | Sheridan |
| 4,484,586 | A | 11/1984 | McMickle et al. |
| 4,495,134 | A | 1/1985 | Ouchi et al. |
| 4,516,972 | A | 5/1985 | Samson |
| 4,531,943 | A | 7/1985 | Van Tassel et al. |
| 4,551,292 | A | 11/1985 | Fletcher et al. |
| 4,557,781 | A | 12/1985 | Hoppie |
| 4,563,181 | A | 1/1986 | Wijayarathna et al. |
| 4,577,543 | A | 3/1986 | Wilson |
| 4,588,398 | A | 5/1986 | Daugherty et al. |
| 4,596,563 | A | 6/1986 | Pande |
| 4,655,762 | A | 4/1987 | Rogers |
| 4,657,024 | A | 4/1987 | Coneys |
| 4,676,229 | A | 6/1987 | Krasnicki et al. |
| 4,684,363 | A | 8/1987 | Ari et al. |
| 4,737,153 | A | 4/1988 | Shimamura et al. |
| 4,737,219 | A | 4/1988 | Taller et al. |
| 4,739,768 | A | 4/1988 | Engelson |
| 4,753,222 | A | 6/1988 | Morishita |
| 4,753,765 | A | 6/1988 | Pande |
| 4,778,550 | A | 10/1988 | Barton et al. |
| 4,806,182 | A | 2/1989 | Rydell et al. |
| 4,817,613 | A | 4/1989 | Jaraczewski et al. |
| 4,826,480 | A | 5/1989 | Diaz et al. |
| 4,830,059 | A | 5/1989 | Silberstang |
| 4,832,681 | A | 5/1989 | Lenck |
| 4,842,590 | A | 6/1989 | Tanabe et al. |
| 4,863,442 | A | 9/1989 | DeMello et al. |
| 4,874,373 | A | 10/1989 | Luther et al. |
| 4,886,506 | A | 12/1989 | Lovgren et al. |
| 4,899,787 | A | 2/1990 | Ouchi et al. |
| 4,944,745 | A | 7/1990 | Sogard et al. |
| 4,950,257 | A | 8/1990 | Hibbs et al. |
| 4,959,067 | A | 9/1990 | Muller |
| 4,981,478 | A | 1/1991 | Evard et al. |
| 4,985,022 | A | 1/1991 | Fearnot et al. |
| 5,035,686 | A | 7/1991 | Crittenden et al. |
| 5,037,404 | A | 8/1991 | Gold et al. |
| 5,057,092 | A | 10/1991 | Webster, Jr. |
| 5,061,257 | A | 10/1991 | Martinez et al. |
| 5,069,674 | A | 12/1991 | Fearnot et al. |
| 5,078,702 | A | 1/1992 | Pomeranz |
| 5,125,913 | A | 6/1992 | Quackenbush |
| 5,160,559 | A | 11/1992 | Scovil et al. |
| 5,165,420 | A | 11/1992 | Strickland |
| 5,167,647 | A | 12/1992 | Wijkamp et al. |
| 5,176,660 | A | 1/1993 | Truckai |
| 5,176,661 | A | 1/1993 | Evard et al. |
| 5,178,158 | A | 1/1993 | de Toledo |
| 5,180,376 | A | 1/1993 | Fischell |
| 5,184,627 | A | 2/1993 | de Toledo |
| 5,188,593 | A | 2/1993 | Martin |
| 5,190,529 | A | 3/1993 | McCrory et al. |
| 5,201,723 | A | 4/1993 | Quinn |
| 5,205,830 | A | 4/1993 | Dassa et al. |
| 5,217,482 | A | 6/1993 | Keith |
| 5,217,555 | A | 6/1993 | Franklin, III et al. |
| 5,221,270 | A | 6/1993 | Parker |
| 5,222,949 | A | 6/1993 | Kaldany |
| 5,234,416 | A | 8/1993 | Macaulay et al. |
| 5,240,537 | A | 8/1993 | Bodicky |
| 5,248,305 | A | 9/1993 | Zdrahala |
| 5,251,640 | A | 10/1993 | Osborne |
| 5,254,107 | A | 10/1993 | Soltesz |
| 5,279,596 | A | 1/1994 | Castaneda et al. |
| 5,292,311 | A | 3/1994 | Cope |
| 5,300,032 | A | 4/1994 | Hibbs et al. |
| 5,304,134 | A * | 4/1994 | Kraus et al. ............... 604/96.01 |
| 5,312,356 | A | 5/1994 | Engelson et al. |
| 5,313,967 | A | 5/1994 | Lieber et al. |
| 5,318,032 | A | 6/1994 | Lonsbusry et al. |
| 5,328,468 | A | 7/1994 | Kaneko et al. |
| 5,330,444 | A | 7/1994 | Webler et al. |
| 5,334,169 | A | 8/1994 | Brown et al. |
| 5,336,205 | A | 8/1994 | Zenzen et al. |
| 5,338,299 | A | 8/1994 | Barlow |
| 5,342,383 | A | 8/1994 | Thomas |
| 5,380,301 | A | 1/1995 | Prichard et al. |
| 5,403,292 | A | 4/1995 | Ju |
| 5,405,338 | A | 4/1995 | Kranys |
| 5,423,773 | A | 6/1995 | Jimenez |
| 5,425,712 | A | 6/1995 | Goodin |
| 5,447,503 | A | 9/1995 | Miller |
| 5,451,209 | A | 9/1995 | Ainsworth et al. |
| 5,454,795 | A | 10/1995 | Samson |
| 5,465,710 | A | 11/1995 | Miyagi et al. |
| 5,492,532 | A * | 2/1996 | Ryan et al. ............... 604/103.09 |
| 5,509,910 | A | 4/1996 | Lunn |
| 5,531,715 | A | 7/1996 | Engelson et al. |
| 5,533,987 | A | 7/1996 | Pray et al. |
| 5,533,988 | A | 7/1996 | Dickerson et al. |
| 5,538,512 | A | 7/1996 | Zenzon et al. |
| 5,538,513 | A | 7/1996 | Okajima |
| 5,545,149 | A | 8/1996 | Brin et al. |
| 5,545,151 | A | 8/1996 | O'Connor et al. |
| 5,558,737 | A | 9/1996 | Brown et al. |
| 5,569,218 | A | 10/1996 | Berg |
| 5,569,220 | A | 10/1996 | Webster, Jr. |
| 5,569,221 | A | 10/1996 | Houser et al. |
| 5,571,089 | A * | 11/1996 | Crocker ............... 604/103.01 |
| 5,599,319 | A | 2/1997 | Stevens |
| 5,603,705 | A | 2/1997 | Berg |
| 5,628,761 | A | 5/1997 | Rizik |
| 5,662,622 | A | 9/1997 | Gore et al. |
| 5,674,208 | A | 10/1997 | Berg et al. |
| 5,680,873 | A | 10/1997 | Berg et al. |
| 5,702,373 | A | 12/1997 | Samson |
| 5,728,063 | A | 3/1998 | Preissman et al. |
| 5,733,248 | A | 3/1998 | Adams et al. |
| 5,755,704 | A | 5/1998 | Lunn |
| 5,759,173 | A | 6/1998 | Preissman et al. |
| 5,762,637 | A | 6/1998 | Berg et al. |
| 5,766,160 | A | 6/1998 | Samson et al. |
| 5,769,819 | A | 6/1998 | Schwab et al. |
| 5,769,830 | A | 6/1998 | Parker |
| 5,782,811 | A | 7/1998 | Samson et al. |
| 5,792,116 | A | 8/1998 | Berg et al. |
| 5,792,124 | A | 8/1998 | Horrigan et al. |
| 5,811,043 | A | 9/1998 | Horrigan et al. |
| 5,820,612 | A | 10/1998 | Berg |
| 5,827,225 | A * | 10/1998 | Ma Schwab ............... 604/96.01 |
| 5,830,181 | A | 11/1998 | Thornton |
| 5,836,925 | A | 11/1998 | Soltesz |
| 5,851,464 | A | 12/1998 | Davila et al. |
| 5,853,400 | A | 12/1998 | Samson |
| 5,855,560 | A | 1/1999 | Idaomi et al. |
| 5,860,963 | A | 1/1999 | Azam et al. |
| 5,865,800 | A | 2/1999 | Mirarchi et al. |
| 5,891,114 | A | 4/1999 | Chien et al. |
| 5,897,537 | A | 4/1999 | Berg et al. |
| 5,911,715 | A | 6/1999 | Berg et al. |
| 5,951,929 | A | 9/1999 | Wilson |
| 5,957,893 | A | 9/1999 | Luther et al. |
| 5,961,485 | A | 10/1999 | Martin |
| 5,964,778 | A | 10/1999 | Fugoso et al. |
| 5,971,975 | A | 10/1999 | Mills et al. |
| 5,997,487 | A | 12/1999 | Kolehmainen et al. |
| 6,017,323 | A | 1/2000 | Chee |
| 6,024,752 | A | 2/2000 | Horn et al. |
| 6,059,770 | A | 5/2000 | Peacock, III et al. |
| 6,102,932 | A | 8/2000 | Kurz |

(56) References Cited

U.S. PATENT DOCUMENTS

| | | |
|---|---|---|
| 6,103,037 A | 8/2000 | Wilson |
| 6,113,579 A | 9/2000 | Eidenschink et al. |
| 6,149,996 A | 11/2000 | Helgerson et al. |
| 6,165,163 A | 12/2000 | Chien et al. |
| 6,168,570 B1 | 1/2001 | Ferrera |
| 6,187,130 B1 | 2/2001 | Berard et al. |
| 6,190,393 B1 | 2/2001 | Bevier et al. |
| 6,210,370 B1 | 4/2001 | Chi-Sing et al. |
| 6,224,610 B1 | 5/2001 | Ferrera |
| 6,245,053 B1 | 6/2001 | Benjamin |
| 6,273,880 B1 | 8/2001 | Berg et al. |
| 6,322,586 B1 | 11/2001 | Monroe et al. |
| 6,325,780 B1 | 12/2001 | Schaible et al. |
| 6,325,790 B1 | 12/2001 | Trotta |
| 6,368,301 B1 | 4/2002 | Hamilton et al. |
| 6,503,353 B1 | 1/2003 | Peterson et al. |
| 6,629,952 B1 | 10/2003 | Chien et al. |
| 6,648,854 B1 | 11/2003 | Patterson et al. |
| 6,652,507 B2 | 11/2003 | Pepin |
| 6,652,508 B2 | 11/2003 | Griffin et al. |
| 6,679,903 B2 | 1/2004 | Kurz |
| 6,790,221 B2 | 9/2004 | Monroe et al. |
| 6,837,869 B2 | 1/2005 | Hamilton et al. |
| 6,852,261 B2 | 2/2005 | Benjamin |
| 6,858,024 B1 | 2/2005 | Berg et al. |
| 6,866,638 B2 | 3/2005 | Dae et al. |
| 6,866,655 B2 | 3/2005 | Hackett |
| 6,881,201 B1 | 4/2005 | Duchamp |
| 7,104,979 B2 | 9/2006 | Jansen et al. |
| 2001/0010247 A1 | 8/2001 | Snow |
| 2002/0156460 A1 | 10/2002 | Ye et al. |
| 2002/0198492 A1* | 12/2002 | Miller et al. ............ 604/96.01 |
| 2003/0009184 A1 | 1/2003 | Pepin |
| 2003/0216642 A1 | 11/2003 | Pepin et al. |
| 2004/0015138 A1 | 1/2004 | Currier et al. |
| 2004/0064130 A1 | 4/2004 | Carter |
| 2004/0097876 A1 | 5/2004 | Shkolnik |
| 2004/0118415 A1 | 6/2004 | Hall et al. |
| 2005/0187536 A1 | 8/2005 | Shelso et al. |
| 2005/0192590 A1 | 9/2005 | Feeley et al. |
| 2005/0288628 A1 | 12/2005 | Jordan et al. |
| 2007/0038239 A1 | 2/2007 | Ritchie |

FOREIGN PATENT DOCUMENTS

| | | |
|---|---|---|
| EP | 0098100 | 1/1984 |
| EP | 0421650 | 4/1991 |
| EP | 0437291 | 12/1993 |
| FR | 2220283 | 10/1974 |
| FR | 2613231 | 10/1988 |
| GB | 2187670 | 9/1987 |
| JP | 2-283346 | 11/1990 |
| JP | 3-23830 | 1/1991 |
| JP | 5-56910 | 3/1993 |
| JP | 5-220225 | 8/1993 |
| WO | WO 93/05842 | 4/1993 |
| WO | WO 93/15785 | 8/1993 |
| WO | WO 96/18431 | 6/1996 |
| WO | WO 96/33763 | 10/1996 |
| WO | WO 99/16494 | 4/1999 |
| WO | WO 99/44666 | 9/1999 |

* cited by examiner

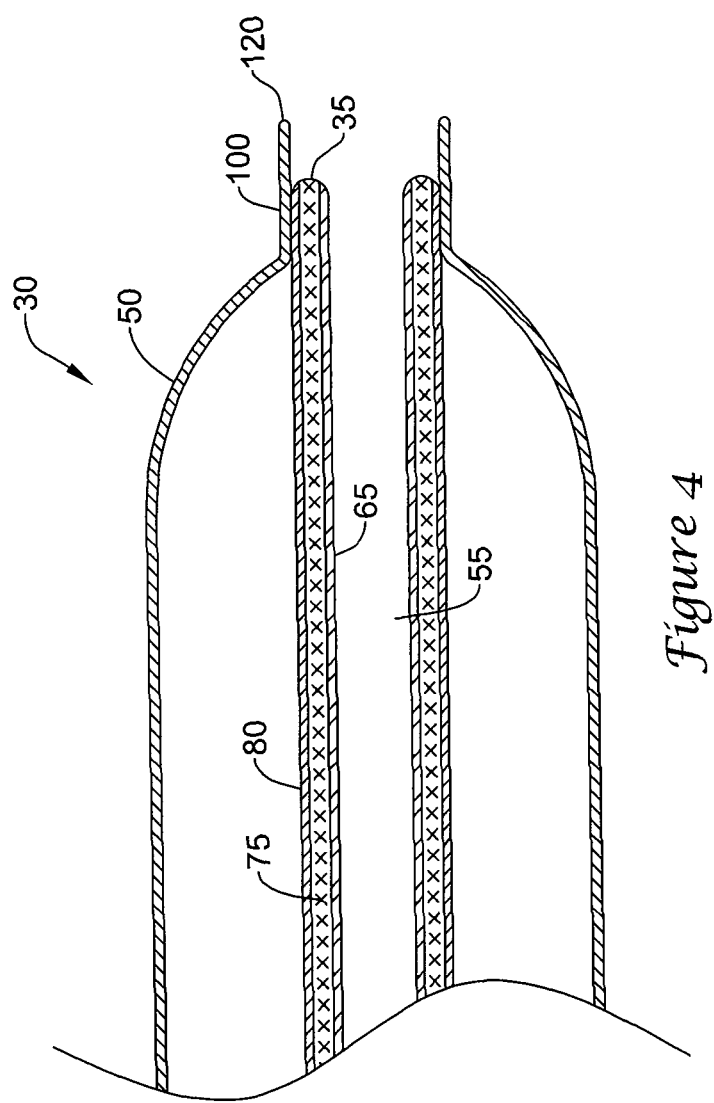

CATHETER HAVING AN ULTRA SOFT TIP AND METHODS FOR MAKING THE SAME

RELATED APPLICATIONS

This application is a continuation of copending U.S. Application Ser. No. 11/009,667, filed Dec. 10, 2004, the entire disclosure of which is incorporated herein by reference.

FIELD OF THE INVENTION

The invention generally relates to intravascular catheters. Specifically, the present invention relates to intravascular balloon catheters including a soft distal tip.

BACKGROUND OF THE INVENTION

Intravascular balloon catheters are used in a wide variety of medical procedures to diagnose and treat vascular abnormalities such as aneurysms, stenotic lesions, intracranial shunts, etc. Such balloon catheters may be used for purposes of dilation, occlusion, flow control, tissue reformation, or the like. Balloons, in particular generally elastic balloons, have also been included on guide catheters to arrest blood flow near a treatment site while another treatment device is extended into a treatment area beyond or distal of the balloon and guide catheter.

Intravascular balloon catheters are commonly navigated through the vasculature to access remote regions of the human body. In order to navigate a vasculature during an intended medical procedure, a catheter must possess opposing characteristics of trackability and flexibility, while retaining a relatively low profile. It is also beneficial that catheters possess a soft distal tip to lessen injury to a vessel wall during navigation through the vasculature.

The hardness or durometer of polymer materials such as those typically used in catheters is commonly measured using the Shore Hardness Test. The Shore Hardness of such materials may be measured by using either the Shore A or Shore D scale. The Shore A scale is used for softer materials, while the Shore D scale is used for harder materials. Both scales range from 0 to 100, where the upper end of the Shore A scale overlaps the lower end of the Shore D scale. For example, a Shore A durometer of 90 is approximately equal to a Shore D durometer of 40. The durometer of the distal tip of exemplary prior art catheters typically are in the range of 35 D to about 70 D. Such distal tips are disclosed in U.S. Pat. No. 6,652,507 issued to Pepin and U.S. Pat. No. 6,368,301 issued to Hamilton et al., the disclosures of each of which are incorporated in their entirety by reference herein.

As catheters are navigated through the vasculature, the distal tip may come into contact with a vessel wall. A hard distal tip formed of the material of the elongate shaft may injure a vessel wall such as a diseased vessel wall. There is a need to provide a catheter with a softer distal tip that can be introduced into a diseased vascular region without causing unnecessary trauma to the vasculature.

SUMMARY OF THE INVENTION

The invention is directed to an intravascular balloon catheter having an ultra soft distal tip. In preferred embodiments, the catheter is a guide catheter including an elastic balloon mounted proximate its distal end. In use, the inflated elastic balloon arrests blood flow near a treatment site while a treatment device extends through the lumen of the guide catheter beyond its distal end to treat the vessel. Accordingly, one embodiment of the invention includes an elongate shaft having a braided reinforcement layer. The reinforcement member can include a metallic or polymeric braided member, single or multiple layers of coiled material or a micromachined tubular member. The micromachined tube can be a hypotube including slots or a spiral cut, for example, to create desired stiffness and flexibility. A polymer layer is disposed about the braided reinforcement layer and may extend distal of the distal end of the braided reinforcement layer. An inflatable balloon is disposed about the distal portion of the elongate shaft and is secured to the polymer layer. A distal portion of the material of the inflatable balloon extends beyond the distal end of the polymer layer to form an ultra soft distal tip. The material of the inflatable balloon and the distal tip is preferably a highly compliant polymer such as a thermoplastic rubber elastomer, providing the catheter with an ultra soft distal tip.

BRIEF DESCRIPTION OF THE DRAWINGS

The invention may be more completely understood in consideration of the following detailed description of various embodiments of the invention in connection with the accompanying drawings, in which:

FIG. 4 is a cross-sectional view showing another embodiment of a distal portion of a catheter in accordance with the invention.

DETAILED DESCRIPTION OF PREFERRED EMBODIMENTS

The following detailed description should be read with reference to the drawings in which similar elements in different drawings are numbered the same. The detailed description and the drawings, which are not necessarily to scale, depict illustrative embodiments and are not intended to limit the scope of the invention.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Figure 1:
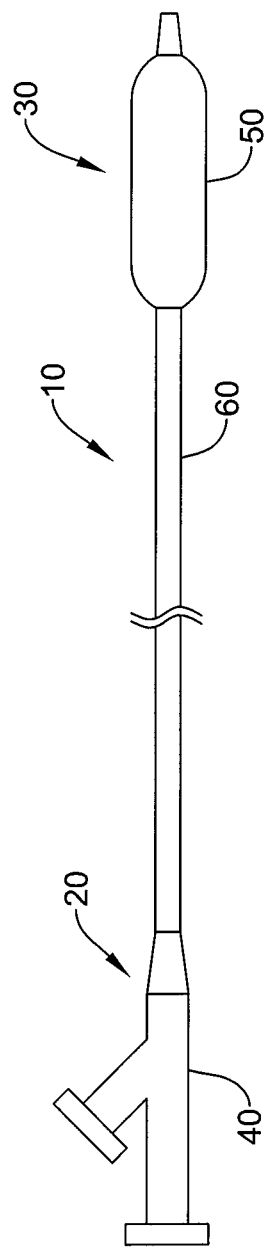
FIG. 1 is a plan view of a balloon catheter in accordance with the invention.

FIG. 1 shows an intravascular balloon catheter in accordance with the invention. Catheter 10 includes a proximal portion 20 and a distal portion 30. The proximal portion 20 may include a hub assembly 40 for communicating with the interior of the catheter. The distal portion 30 may include an expandable balloon 50 for use during a medical procedure. An elongate shaft 60 may extend from the proximal portion 20 to the distal portion 30.

Figure 2:
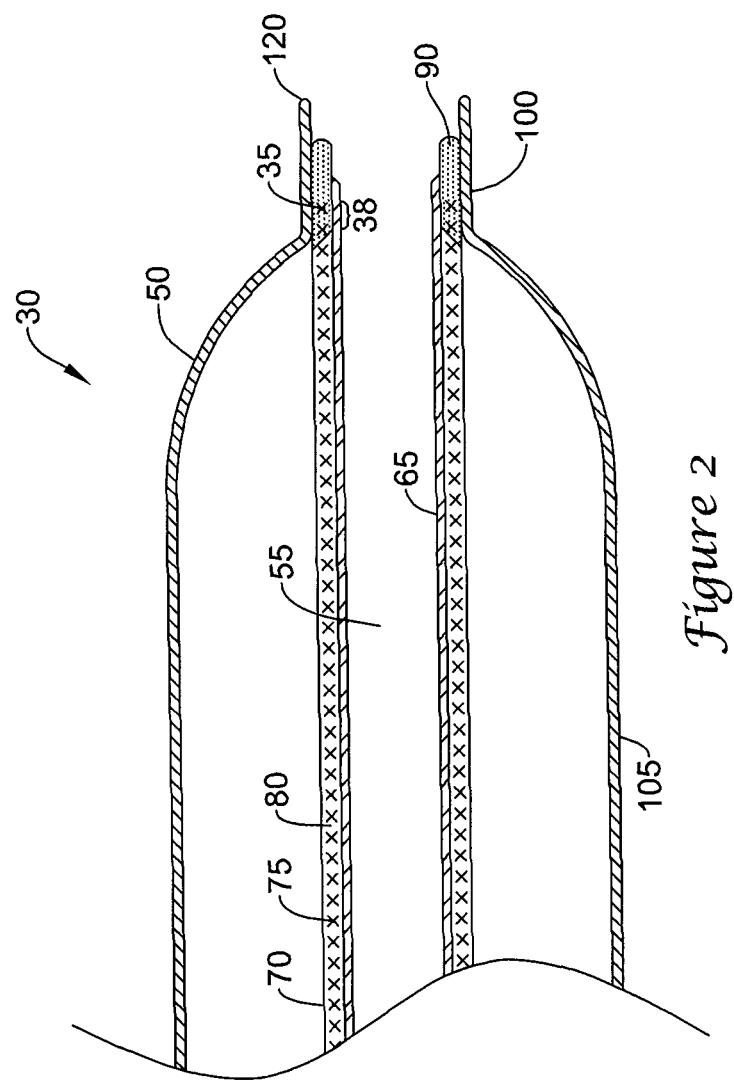
FIG. 2 is a cross-sectional view of the distal portion of a catheter in accordance with the invention.

FIG. 2 shows a distal portion of a catheter in accordance with the invention. Elongate shaft 60 includes a reinforcement member 70 which is depicted for the present embodiment as a braided member 75. It is, however, recognized that the reinforcement member could include single or multiple layers of coiled or helically wrapped material. Alternatively, a micromachined tubular member could be utilized, for example, a slotted hypotube or a spiral cut hypotube. The reinforcement member 70, such as braided member 75 may extend substantially the length of the elongate shaft 60. The braided member 75 may be formed of materials such as metals, metal alloys, polymers, metal-polymer composites, or other suitable materials. Some examples of some suitable materials may include stainless steels (e.g., 304v stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymer material such as a high performance polymer, or other suitable materials, and the like.

The braided member 75 may be covered with a polymer layer 80. Polymer layer 80 may substantially permeate the braided member 75, such that braid interstices are substantially filled with the polymer of the polymer layer 80. Alternatively or additionally, the polymer layer 80 may encase the braided member 75, such that the polymer layer 80 forms a discrete layer over the braided member 75. The polymer layer 80 may be formed of a flexible material such as high-density polyethylene (HDPE), low-density polyethylene (LDPE), silicone, fluoropolymer, liquid crystal polymer (LCP), polyimide, polyamide, polyester, polyethylene (PE), polypropylene, polyvinyl chloride (PVC), polyfluorocarbon, polyurethane, polysulfone, ethyl vinyl acetate (EVA), polyether block amide (PEBAX), styrene-ethylene/butylenes-styrene (SEBS), styrene-butadiene-styrene (SBS), polyethylene terephthalate (PET), and their mixtures, alloys, blends, copolymers, and block copolymers. Preferably, polymer layer 80 may comprise a thermoplastic polyester elastomer having superior flexibility and strength characteristics, such as Hytrel® available from DuPont.

The distal end 35 of the braided member 75 may include a segment 38 free of the polymer layer 80. Polymer layer 80 may be stripped from the segment 38 during a manufacturing process or polymer layer 80 may be disposed proximal of segment 38 prior to securing polymer layer 80 to the braided member 75. The distal segment 38 may extend a few millimeters. Preferably, segment 38 may be between about 1.0 and about 2.0 millimeters in length.

A polymer sleeve 90 may be disposed about segment 38 of the braided member 75. Polymer sleeve 90 may include a different polymer than that of the polymer layer 80. Polymer sleeve 90 may include a low-density polyethylene (LDPE). Polymer sleeve 90 preferably provides a strong bonding substrate for the material of the balloon 50, whereas the material of the balloon 50 may not be as readily bondable to the polymer layer 80. A proximal portion of the polymer sleeve 90 may be disposed about and secured to the braided member 75. Polymer sleeve 90 may permeate the interstices of braided member 75, or polymer sleeve 90 may encase the distal segment 38 of the braided member 75 forming a discrete layer. A distal portion of the polymer sleeve 90 may extend distal of the distal end 35 of the braided member 75 providing a transition in flexibility of the distal end of the catheter 10.

A balloon 50 is disposed about a distal portion of the elongate shaft 60. The balloon 50 may include a proximal waist portion (not shown), a distal waist portion 100, and an intermediate portion 105. The balloon 50 may include a compliant material, such as a thermoplastic rubber elastomer. Preferably, balloon 50 comprises ChronoPrene™, available from CardioTech International, Inc. ChronoPrene™ is a biocompatible elastomeric material having good surface smoothness and excellent elasticity, and may be processed by conventional melt processing methods. ChronoPrene™ has a durometer hardness of 5-40 Shore A making it an ultra soft material. ChronoPrene™ is readily bondable with low-density polyethylene (LDPE), such as may be used in the polymer sleeve 90. The distal waist portion 100 of the balloon 50 may be bonded to the polymer sleeve 90.

The distal waist portion 100 extends distal of the polymer sleeve 90 to form an ultra soft tip 120. The ultra soft tip 120 includes the thermoplastic rubber elastomer of the balloon, thus the ultra soft tip 120 may have a durometer hardness of 5-40 Shore A. The ultra soft tip 120 may extend distal of the polymer sleeve 90. Preferably, ultra soft tip 120 extends less than 1.0 millimeters beyond the polymer sleeve 90 to prevent catheter lumen closure or diameter restriction at the distal tip.

An inner liner 65 may be disposed within the lumen 55 of the reinforcement layer 70. The inner liner 65 may extend substantially the length of the catheter shaft or may extend any length thereof. As shown in FIG. 2, the inner liner 65 may end proximal of the distal end of polymer sleeve 90. Preferably inner liner 65 extends distal of the distal end of braided member 75. Such a configuration creates a step-wise transition from the inner liner 65, to the polymer sleeve 90, to the ultra soft tip 120 created by the distal extension of the distal balloon waist 100. Such a multi-step, step-wise transition creates a region near the distal tip having a multi-step reduction in hardness. Inner liner 65 may create a lubricious surface having a low frictional coefficient in order to facilitate introduction and advancement of a medical device such as a guidewire or aneurysm treatment catheter (for example, a coil delivery catheter) through the lumen 55. Inner liner 65 may include a polymer material such as fluorinated polyethylene, or the like. Preferably, inner liner 65 includes a polytetrafluoroethylene, such as Teflon® available from DuPont.

Figure 3:
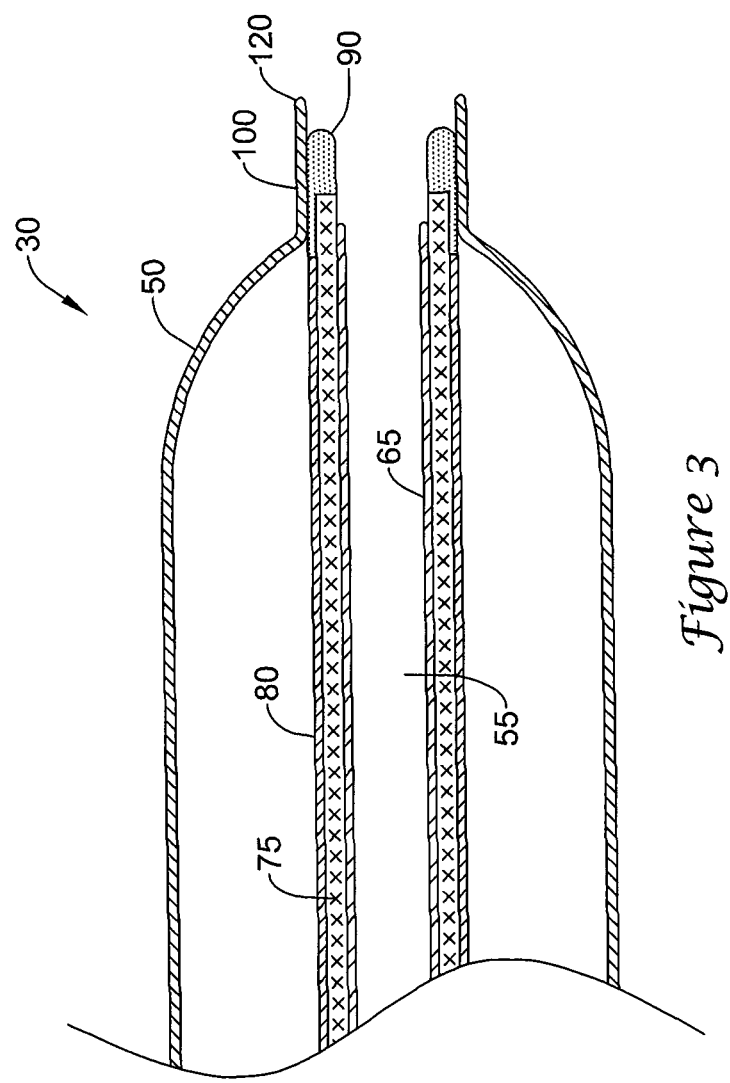
FIG. 3 is a cross-sectional view showing another embodiment of a distal portion of a catheter in accordance with the invention.

FIG. 3 shows an alternate embodiment of a distal tip in accordance with the invention. As shown in FIG. 3, polymer layer 80 may be a discrete layer disposed about the braided member 75. Polymer sleeve 90 may abut the polymer layer 80 forming an interface and extend distal of the distal end of braided member 75. The distal waist portion 100 of balloon 50 extends distal of the polymer sleeve 90 to form an ultra soft distal tip 120.

As shown in FIG. 4, the polymer layer 80 may extend substantially the entire length of the braided member 75. The polymer layer 80 and the inner liner 65 may co-terminate at the distal end 35 of the braided member 75. The distal waist portion 100 of balloon 50 may be bonded to the polymer layer 80 at the distal end of elongate shaft 60. The distal waist portion 100 of balloon 50 may extend distal of the distal end 35 of the braided member 75, forming an ultra soft distal tip 120 having a durometer of between about 5 A and about 40 A.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What we claim is:
1. A method of forming a catheter, the method comprising:
providing an elongate shaft including a braided reinforcement member having a proximal end, a distal end and a lumen extending therethrough;

disposing an outer layer about at least a portion of the braided reinforcement member, the outer layer having a proximal end and a distal end;

wherein disposing an outer layer about at least a portion of the braided reinforcement member includes disposing the outer layer so that the distal end of the outer layer is positioned proximal of the distal end of the reinforcement member;

disposing a sleeve having a proximal end and a distal end about a portion of the braided reinforcement member distal of the distal end of the outer layer, the sleeve extending distal of the distal end of the braided reinforcement member;

disposing an inflatable balloon having a proximal waist segment and a distal waist segment about a distal portion of the elongate shaft, wherein the distal waist segment is disposed about the sleeve and a portion of the distal waist segment extends distal of the distal end of the sleeve;

forming a distal tip with the portion of the distal waist segment extending distal of the distal end of the sleeve; and;

wherein a material bonding strength between the inflatable balloon and the sleeve is greater than a material bonding strength between the inflatable balloon and the outer layer.

2. The method of claim 1, further comprising:
disposing an inner layer within at least a portion of the lumen of the braided reinforcement member, the inner layer having a distal end disposed proximal of the distal end of the sleeve.

3. The method of claim 1, wherein the distal tip is an ultra soft tip.

4. The method of claim 3, wherein the ultra soft tip has a durometer hardness of between about 5 A and about 40 A.

5. The method of claim 1, wherein the outer layer includes a thermoplastic polyester elastomer.

6. The method of claim 1, wherein the sleeve includes a low-density polyethylene (LDPE).

7. The method of forming a catheter according to claim 1, wherein the inflatable balloon includes a thermoplastic rubber elastomer.

8. A method of making a catheter, the method comprising:
providing an elongate shaft including a reinforcement member having a proximal end and a distal end;
disposing an outer layer about at least a portion of the reinforcement member, the outer layer having a proximal end and a distal end, the distal end of the outer layer terminating proximal of the distal end of the reinforcement member;
disposing a distal extension about a distal portion of the reinforcement member, the distal extension having a proximal end and a distal end, the proximal end of the distal extension disposed distal of the distal end of the outer layer;
disposing an inflatable member about the elongate shaft, the inflatable member including a proximal waist section and a distal waist section, the distal waist section secured to the distal extension, wherein a portion of the distal waist section extends distal of the distal end of the distal extension; and
wherein a material bonding strength between the inflatable member and the distal extension is greater than a material bonding strength between the inflatable member and the outer layer.

9. The method of claim 8, wherein the distal extension comprises a first polymer material and the outer layer comprises a second polymer material different from the first polymer material, and wherein a material bonding strength between the inflatable member and the first polymer material is greater than a material bonding strength between the inflatable member and the second polymer material.

10. The method of claim 8, wherein the proximal end of the distal extension is adjacent the distal end of the reinforcement member.

11. The method of claim 8, wherein the portion of the distal waist section extending distal of the distal end of the distal extension forms a distal tip.

12. The method of claim 11, wherein the distal tip has a durometer hardness of between about 5 A to about 40 A.

13. The method of claim 8, further comprising disposing an inner layer within at least a portion of the reinforcement member.

14. The method of claim 8, wherein the outer layer includes a thermoplastic polyester elastomer.

15. The method of claim 8, wherein the distal extension includes a low-density polyethylene (LDPE).

16. The method of claim 8, wherein the inflatable member includes a thermoplastic rubber elastomer.

17. A method of making a catheter, the method comprising:
providing an elongate shaft including a proximal portion and a distal extension extending distally from the proximal portion, wherein the distal extension comprises a first polymer material and the proximal portion comprises a second polymer material different from the first polymer material;
wherein the shaft includes a reinforcing member that extends along the proximal portion and along the distal portion and an outer layer disposed about at least a portion of the reinforcement member, the outer layer having a proximal end and a distal end, the distal end of the outer layer terminating proximal of the distal end of the reinforcement member;
disposing an inflatable member about the elongate shaft, the inflatable member including a proximal waist section and a distal waist section, the distal waist section secured to the distal extension and a portion of the distal waist section extends distal of the distal end of the distal extension; and
wherein a material bonding strength between the inflatable member and the distal extension is greater than a material bonding strength between the inflatable member and the outer layer.

18. The method of claim 17, wherein the first polymer material of the distal extension provides a strong bonding substrate for a material of the balloon, whereas the material of the balloon is not as readily bondable to the second polymer material of the proximal portion.

* * * * *